United States Patent [19]

Fisch et al.

[11] Patent Number: 4,831,268

[45] Date of Patent: May 16, 1989

[54] METHOD FOR THE PHYSIOLOGICALLY & THERAPEUTICALLY EFFECTIVE IRRADIATION OF CORPOREAL VENOUS BLOOD

[75] Inventors: Joachim Fisch, Ilmenau; Hans-Richard Kost, Hildburghausen; Manfred Riemann, Ilmenau; Jör Sonnemann, Ilmenau; Gerda Fisch, Ilmenau, all of German Democratic Rep.

[73] Assignee: VEB Elektro-und Metallgeräte Ilmenau, Ilmenau, German Democratic Rep.

[21] Appl. No.: 271,343

[22] Filed: Nov. 10, 1988

Related U.S. Application Data

[63] Continuation of Ser. No. 169,071, Mar. 15, 1988, abandoned, which is a continuation of Ser. No. 841,972, Mar. 20, 1986, abandoned.

[30] Foreign Application Priority Data

Mar. 20, 1985 [DD] German Democratic Rep. ... 274282

[51] Int. Cl.$^4$ .............. G01N 23/12; A61L 2/00; H01J 37/00
[52] U.S. Cl. .............. 250/432 R; 250/504 R; 250/435; 422/21
[58] Field of Search ............ 250/492.1, 432 R, 504 R, 250/435, 431, 503.1, 453.1; 422/24, 44; 128/395, 397, 398; 604/4

[56] References Cited

U.S. PATENT DOCUMENTS

| | | | |
|---|---|---|---|
| 3,466,443 | 9/1969 | Roesler et al. | 250/504 R |
| 4,321,918 | 3/1982 | Clark | 604/4 |
| 4,467,206 | 8/1984 | Taylor et al. | 250/435 |
| 4,591,724 | 5/1986 | Fuse et al. | 250/492.1 |
| 4,591,958 | 5/1986 | Lamboo | 362/219 |

FOREIGN PATENT DOCUMENTS

| | | | |
|---|---|---|---|
| 2926523 | 1/1981 | Fed. Rep. of Germany | 422/44 |
| 1056512 | 3/1954 | France | 250/432 R |
| 1189979 | 10/1959 | France | 250/493.1 |
| 2555567 | 5/1985 | France | 250/432 R |
| 0199296 | 11/1984 | Japan | 250/504 R |

Primary Examiner—Bruce C. Anderson
Attorney, Agent, or Firm—Schweitzer & Cornman

[57] ABSTRACT

A method for the radiation of corporeal blood is described with which it is possible to prevent arteriosclerosis related heart and vascular diseases due to disturbances in the fat exchange, or to successfully fight such diseases, without exposing the blood to photosensibilators or without the necessity of additional corporeal activity, or a special diet. The apparatus is easily transportable, indepedent from electrical supply lines and may, for example, be operated from the energy obtained from a car battery. A radiation spectrum is used, which employs optical radiation types, which are available on the surface of the earth in nature, so that damages to the organism in principle are prevented.

5 Claims, 2 Drawing Sheets

METHOD FOR THE PHYSIOLOGICALLY & THERAPEUTICALLY EFFECTIVE IRRADIATION OF CORPOREAL VENOUS BLOOD

This is a continuing application of U.S. Ser. No. 169,071, filed on Mar. 15, 1988, now abandoned, which is a continuation of application for United States Letters Patent Ser. No. 841,972, filed on Mar. 20, 1986, now abandoned.

FIELD OF THE INVENTION

The present invention relates to an apparatus with the help of which the irradiation of corporeal venous blood, especially the UVA region and in the blue light region becomes possible. Such apparatuses and devices especially for blood processing have been introduced since some time and used in the medical profession. The users firmly believe in the physiologically and therapeutically effective blood processing.

The object of the subsequently described technical solution resides in that the blood should be influenced in such a manner that by an increased oxygen acceptance the regenerating processes which go on in the body, such as the fat exchange, should be accelerated. During this certain disturbed biological parameters, such as the low Density Lipoproteins should be changed to High Density Lipoprotein-cholestrol in a positive sense and in favor of the vascular protective balance (HDL-C).

DESCRIPTION OF THE PRIOR ART

There have been apparatuses and devices known with which the oxygen/ozone gas mixture is applied subcutaneous, intramuscularly, intraveneously or by insufflation. For example, in East German Pat. No. 14,127 a device for the oxygen enrichment of a continuously flowing blood stream is described, in which by foaming-up the blood by oxygen the upper surface thereof is increased.

Futhermore, devices and apparatuses are known in which the blood in a quartz glass vessel (cell or bulb) is flowed by a UV radiator for purposes of radiation, such as described in West German Pat. Nos. 1,065,140 and 1,071,291, as well as in West German Laid-Open Application No. 2,926,523. Such apparatuses require a very large technical layout for the apparatus, and wherein the apparatus becomes reused as a matter of rule. The disadvantage resides in that the blood may become overheated and the disinfecting requirements are very complex and there is a danger of tranferring and spreading of germs (virus, hepatitis, aids, etc.), since no disposable material is used by them.

There are also devices known for some time, in which the blood becomes foamed-up by means of oxygen and it is also subjected to an ultraviolet radiation. For example, in West German Pat. No. 957,877 and in West German Laid -Open Application No. 1,215,867 devices are described for the processing of blood, blood plasma or similar materials, with oxygen and also with ultraviolet radiation.

Also with them complex devices are required, and all have the already known and above-mentioned disadvantages. In addition, due to the increased upper surface by the foaming, the intensity of the radiation becomes uncontrollable which may lead to cell or gene damages.

In U.S. Pat. Nos. 4,321,919 and 4,464,166 a method is described in which corporeal blood of the person under test is passed by a pump through a radiation chamber and through a centrifuge and again back into the body. The sterilization requirements must be observed during this to an extremely high degree and the technical layout of the apparatus is considerable. In addition, all the above-mentioned disadvantages are present also here.

A third solution is described in West German Laid-Open Application No. 2,943,310A1 according to which by means of a light conducting cable introduced by puncturing a UV-radiation is introduced into the blood vessel system and thereby a biophysical effect is attained. The main disadvantage of such procedure resides in the above-mentioned possible transfer of germs, due to the face that the sterilization of the reuseable light cable is complicated.

All the so far mentioned apparatuses and devices require a considerable technical and medical effort. Economical, personnel and sterilization problems considerably limit their use. Contaminations or transfer of germs in the blood in many of the procedures cannot be avoided. A false dozing or metering of the gas used in the foaming-up of the blood, for example, oxygen and also of the UV radiation, due to human error, may lead to life endangering complications, such as embolism, gene or cell destruction. The cleaning and the sterilization of the known apparatus and devices is very complicated. In the above-described known procedures for blood irradiation usually UVC radiators are used, which have a main emission line of 253.7 nm. Such wavelength so far has been reserved for essential therapeutical treatments. Latest research shows that the relatively hard, energy rich UVC radiation in the event of excessive doeses, may lead to damages of the biological cells and tissues. Such damages may lead to deterioration of the blood producing system (leukemia) and other inheritable damages.

SUMMARY OF THE INVENTION

It is, therefore, an object of the present invention to provide an apparatus, which:

Does not present a danger for the person under testing and employs mainly optical radiation, predominantly in the UVA and blue light regions;

From the hygienic viewpoint it enables substantial improvements and assures the observation of the legal requirements;

Its technical reliability is substantially improved and can be operated from a conventional energy supply as well as from a low voltage source;

It is small, light, independent from the conventional energy supply and thereby it is mobile;

It is inexpensive to make and possesses a very high serviceability.

A further object of the present invention resides in the provision of an apparatus, in which a radiation is used which is in the radiation range of the sun radiation available on the surface of the earth and in which an exact metering of the radiated quantity is assured.

According to a further object of the present invention the oxygen reception is improved without foaming-up or additional corporeal activity and thereby the peripheral microcirculation is improved, thereby any fat exchange disturbances of the body are positively influenced.

Furthermore, the radiation strength in each radiation period must be uniform and the blood should be brought in contact only with disposable materials.

The apparatus for the physiological and therapeutical optical irradiation of corporeal venous blood according to the present invention comprises a radiator, which emits radiation mainly in the wavelength region of 320 nm to 600 nm.

A hose which is arranged substantially parallel to such in radiator is made from a disposable material will be flown through by venous blood treated with sodium citrate or another type of anticoagulant, and exposed to radiation. By the reflections it will assured that the hose becomes uniformly radiated from all sides with the blood flowing therethrough. It is therefore preferred that the radiator as far as the hose be disposed in the focus of a reflector formed by conical sections. The irradiator, the hose and the reflectors are arranged in a housing having a cover and supported therein by known securing means. The hose is tightly secured or tensed in the housing in clamping devices which may take the form of conical slots, to avoid any slack in it. The flow-rate of the blood can be regulated by means of a hose clamp provided on the housing. Around the radiator there is provided is sleeve-like telescope arrangement, with which by displacing a telescoping sleeve, the length of the radiation emitting portion of the irradiator can be adjusted.

In addition the intensity of the radiation of the radiator can be adjusted by adjusting the applied voltage. For this reason, outside of the housing in the supply cable a switch, for example, of the type EVG UVAP1 manufactured by the Technical High School in Ilmenau, is arranged.

For radiation preferably a xenon lamp, argon lamp or a mercury-low pressure discharge lamp of the type L S4 of Narva I1., can be used.

In addition it is possible to vary the frequency spectrum by providing suitable luminous materials such as the three-band luminous materials and with the help of varying the blue component a irradiator which emits an unsuitable or too wide frequency spectrum can be adjusted to the desired frequency range of 320 nm to 600 n.

The quantity of the irradiation on the blood can be varied by various means. The length of the irradiated hose section can be varied with the help of the telescopic arrangement placed on the radiator, as well as the intensity of the irradiation can be controlled by changing the high frequency input to the irradiation and furthermore the quantity of the blood flowing through the hose can be adjusted by a conventional hose clamp or other similar means by narrowing the cross section of the hose. It can be understood that by changing all three means, the irradiation dose to which the blood is exposed, can be exactly set, whereby the mentioned three means are preferably varied in the following quantities:

Radiation intensity: between 1 mWcm$^{-2}$ and 10 mWcm$^{-2}$;
Length of the irradiated hose section: 1 cm to 30 cm;
Flow-rate of the blood: 20 to 80 drops per minute.

With the help of the apparatus according to the present invention it becomes possible to prevent arteriosclerotic heart or blood vessel deteriorations caused by disturbances in the fat exchange, expecially they could be effectively counted, without adding to the blood photosensibilators, such as Psoralens, described by Edelson. During this additional corporeal activity and dietectic measures are desirable, however, they are not absolutely required. Also by using disposable materials, the spreading of infectious diseases, such as aids and hepatitis B is completely eliminated.

The employed radiation type completely avoids any DNA damage or the inducement of cancer, since only optical radiation is used, which is available on the surface of the earth in nature. At the same time the radiation is performed in a frequency region in which the erythrose will absorb the offered radiation to a maximal extent.

The apparatus is easily transportable, hygienic and can be set up in any situation without relying on the current supply, that is, it can have its energy supply from a car battery. It is inexpensive to manufacture and requires small material layout and it is also easy to service.

DESCRIPTION OF THE DRAWINGS

The invention will be explained with reference to the attached drawings, in which.

DESCRIPTION OF SPECIFIC EMBODIMENTS

The following embodiment serves only for illustration and for a better understanding of the invention, and the invention itself should not be limited thereby since it represents only one possible form of illustration.

Figure 1:
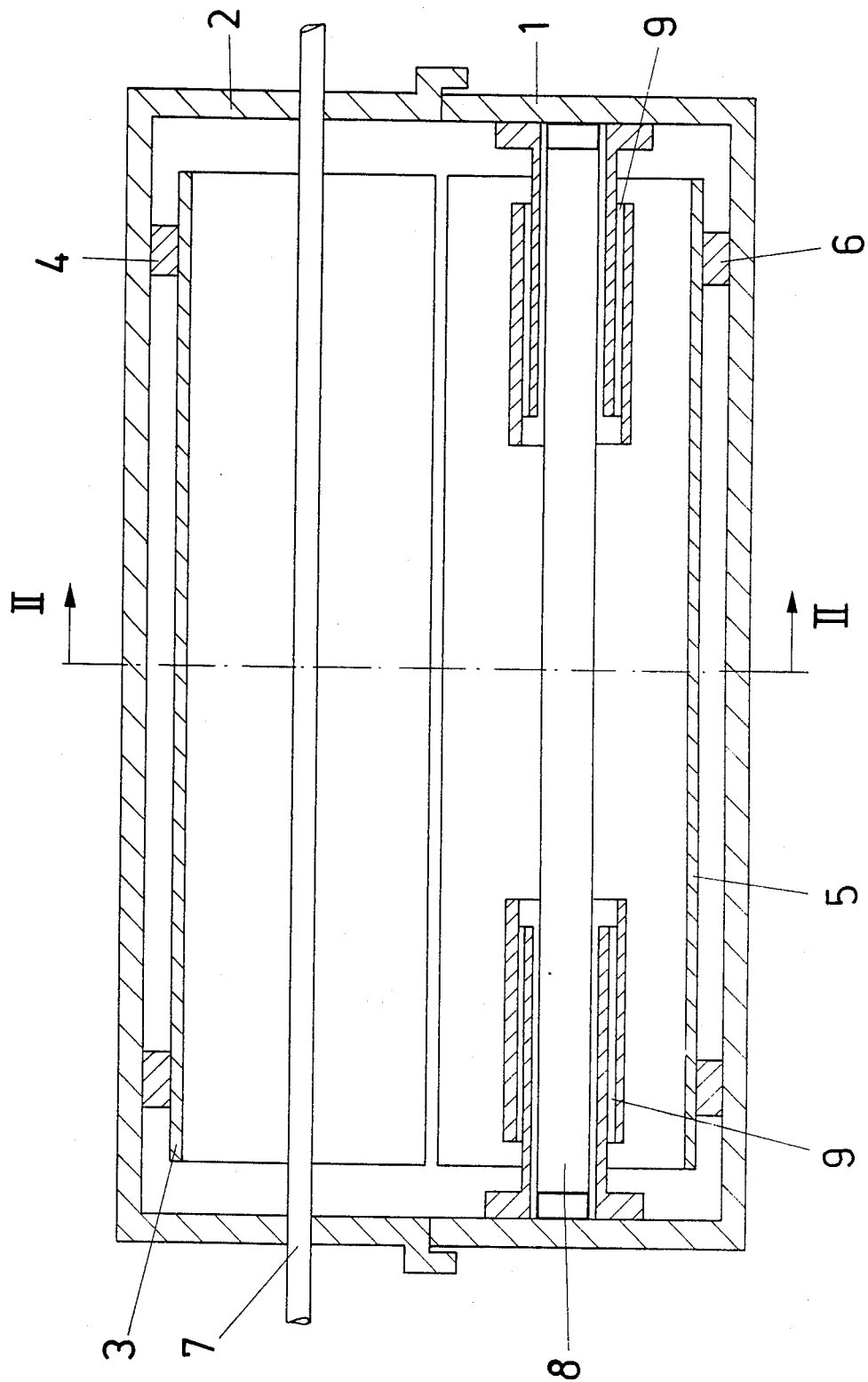
FIG. 1 is a schematic sideview of the apparatus according to the present invention, in section.
Figure 2:
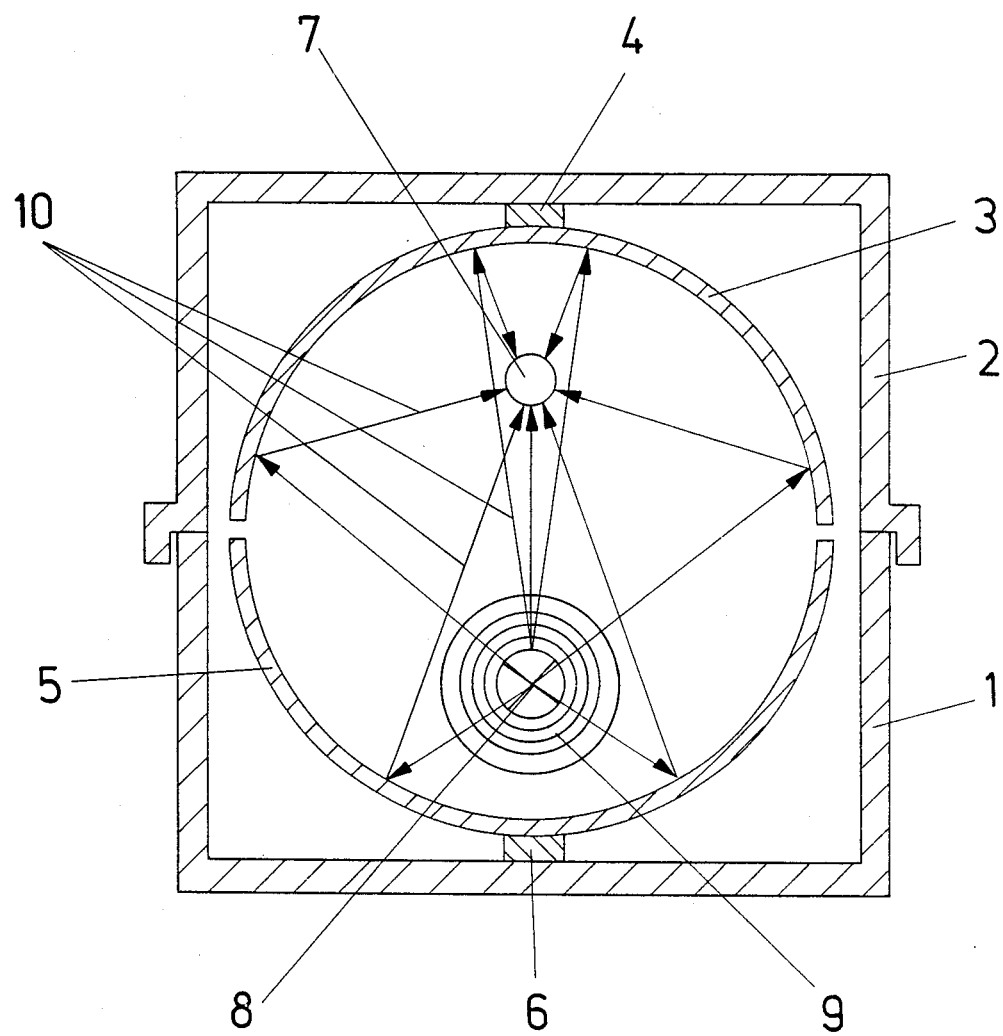
FIG. 2 is a schematic sectional illustration along the line II—II in FIG. 1.

A possible embodiment of the present invention illustrated in FIG. 1 and FIG. 2 shows a housing 1, which can be closed by a cover 2. In cover 2 there is a reflector 3 secured by any well known not illustrated in detail means 4, such as screws or rivets provided with rubber backing. A further similar reflector 5 is secured within the housing 1 with similar means 6. In the focus of the reflectors 3 provided in the cover 2 a PVC hose 7 is arranged, which is supported by means of suitable securing elements and is spanned or tensioned by spring means so that it will lie exactly in focus substantially along the entire length of the reflector. The securing elements and the springs have been omitted for improving the understanding of the schematic illustration. In the focus of the reflector 2 provided in the housing 1 a irradiator 8 is arranged, the radiation emitting length of which can be adjusted with th help of a telescopic arrangement 9, which is arranged in a pipe-like fashion about the irradiator 8. The radiator 8 is operated with the help of an electronic switching device (not illustrate), for example the EVG UVAB1 manufactured by the Technical High School Ilmenau, having a variable HF output, and which can be placed in the housing 1, 2 or outside of the housing 1, 2 or also as an intermediate element inserted in the supply cable.

The venous blood becomes guided through the PVC hose 7 through the cover 2 of the housing 1, 2 along the irradiator 8. The length of the hose section which is to be radiated and thereby the amount of the radiation as well as the exposure of the blood to radiation can be set with the help of the telescopic arrangement 9 by reducing the possible length of emission of the irradiator 8. By arranging the PVC hose 7 and the irradiator 8 in the focal point of the reflectors 3, 5, it is attained that a maximum value of the radiation emitted by the irradiator 8 will be directed onto the PVC hose 7. By an appropriate dimensioning of the housing 1 and of the cover 2, one will attain that there will be a desired distance or spacing present between the irradiator 8 and the PVC hose 7 in an exact amount, whenever the cover 2 is seated on the housing 1. The reflectors 3, 5 are shaped and a curvature is formed in such a manner, that at such spacing the PVC hose 7 will receive the largest amount of radiation. The reflectors are also shaped n such a manner that the most possible rays of radiation 10 will be directed from irradiator 8 onto the PVC hose 7. The possible paths of the radiated rays 10 are schematically illustrated in FIG. 2.

For a switching device preferably a known serial-type device is used (for example, the type known as EVG UVAB1 manufactured by the Technical High School in Ilmenau), which can be operated with low voltage of 42V or from the regular current supply, for example, 110/220V. The device in such form is transportable, it is easy to be handled and used. For hygienic reasons the PVC hose 7 is manufactured as a disposable material, such as the blood transfusion device MLW Lichtenberg and becomes destroyed after use.

It can be seen that it is also possible to arrange the telescopic arrangement 9 only on one side of the housing, or to replace it by a different type of cover, such as a rotatable pipe-like hood with a spiral-shaped edge, which is arranged surrounding irradiator 8 and by being rotated it can change the free radiating length of the irradiator 8.

The above-noted embodiment describes only a possible form of realization of the invention only for better information and should not limit the scope of the invention to such embodiment alone. The scope of protection should be defined by the claims. Variations which would be obvious for an expert in the field and limitations, such as, the reflectors on the radiator or on the ends of the hose between the housing elements, should lie within the scope of the claims defining the invention.

What is claimed is:

1. A process for physiological and therapeutic treatment of venous blood from a body, which comprises (a) introducing the blood into an apparatus having a blood conducting tube of medically acceptable disposable material, at least on elongated radiator for emitting electromagnetic radiation, a reflector for distributing the radiation of said radiator substantially about said tube, and means for controlling the radiation that reaches said tube from said radiator, (b) conducting the blood through said blood conducting tube at a flow rate of from about 20 drops/minute to about 80 drops/minute, and (c) irradiating the blood in the blood conducting tube with radiation from said radiator at an intensity of from about 1 mWcm$^{-2}$ to about 10 mWcm$^{-2}$ in the wavelength range of from about 320 nm to about 600 nm.

2. The process of claim 1, wherein the length of the blood conducting tube that is exposed to the electromagnetic radiation is from about 1 cm to about 30 cm.

3. The process of claim 1, wherein said means for controlling the radiation comprises telescoping adjustable tubular shrouds.

4. The process of claim 1, wherein the spectral emission of said radiator is adjusted by a coating of luminous material on said radiator.

5. The process of claim 1, wherein said radiator is a xenon lampa.

* * * * *